United States Patent [19]

Bajard et al.

[11] Patent Number: 4,622,642
[45] Date of Patent: Nov. 11, 1986

[54] BATCH INTERFERENCE GRANULOMETRIC PROCESS PARTICULARLY APPLICABLE TO POLY-DISPERSED BIOLOGICAL PARTICLES

[76] Inventors: Jean Bajard, "Le Vallon", 5, rue Charles Baudelaire, 67370 Griesheim-Sur-Souffel; Jean-Paul Méric, 10, rue du Docteur Roux, 75015 Paris, both of France

[21] Appl. No.: 463,576

[22] Filed: Feb. 3, 1983

[30] Foreign Application Priority Data

Feb. 3, 1982 [FR] France .................. 82 01843

[51] Int. Cl.$^4$ .......................................... G01N 15/02
[52] U.S. Cl. ....................................... 364/555; 356/335
[58] Field of Search ............... 364/555, 416, 525; 377/10; 356/335, 39, 338; 250/574

[56] References Cited

U.S. PATENT DOCUMENTS

| | | | |
|---|---|---|---|
| 3,941,479 | 3/1976 | Whitehead | 364/555 X |
| 4,191,940 | 3/1980 | Polcyn et al. | 364/416 X |
| 4,233,664 | 11/1980 | Grandchamp | 364/555 |
| 4,242,730 | 12/1980 | Golias et al. | 364/416 |
| 4,318,180 | 3/1982 | Lundqvist et al. | 364/555 |
| 4,419,879 | 12/1983 | Bush et al. | 364/555 X |

FOREIGN PATENT DOCUMENTS 1417691 12/1975 United Kingdom .

OTHER PUBLICATIONS

"Measurement of Particle Size, Number Density and Velocity Using a Laser Interferometer", by W. M. Farmer–Applied Optics Nov. 1972, vol. 11, No. 11 pp. 2603–2612.

"Measurement of Particle Size & Refractive Index Using Crossed Beam Laser Anemometry", by M. S. Atakan et al.–1261 Journal of Physics D. Applied Physics, vol. 15 (1982), Jan. No. 1 pp. 1–13.

"Method for Measuring the Size and Velocity of Spheres by Dual–Beam Light–Scatter Interferometry", by W. D. Bachalo 2219 Applied Optics (Feb. 1980) vol. 19, No. 3 Feb. 1, 1980.

"Mie Theory Calculations: New Progress, with Emphasis on Particle Sizing" by G. Gouesbes.

Primary Examiner—Edward J. Wise
Attorney, Agent, or Firm—Young & Thompson

[57] ABSTRACT

A process for batch interferential granulometry applicable particularly to poly-dispersed biological particles. The process is characterized in that the positioning of the angular measurement regions is selected according to the criteria of representativity of the signals obtained with respect to the given granulometry sought, particularly for their alternative components, and in that the processing of the signals comprises successively a harmonic Fourier analysis of their alternative components, and the use of the results of this analysis in a computation leading to the parameters sought, namely, the numbers, mean dimensions, and granulometric distribution of the analyzed particles.

4 Claims, 3 Drawing Figures

View from above front view $F_1 = \quad X \quad \delta = 3{,}2 \mu m$ $F_2 = \quad Y$ $F_3 = \quad Z$ $\delta = 25 \mu m$ $\delta = 25 \mu m$

BATCH INTERFERENCE GRANULOMETRIC PROCESS PARTICULARLY APPLICABLE TO POLY-DISPERSED BIOLOGICAL PARTICLES

The present invention relates to the field of the granulometric analysis of particles, and has for its object a process for batch interference granulometry, applicable particularly to poly-dispersed biological particles.

At present, the methods for the determination of granulometric characteristics, such as number, dimensions, and the granulometric curve of a group of particles in suspension in a fluid are generally of two categories, namely, flow processes, and batch processes.

In the flow processes, the particles pass one by one through a measurement cell that furnishes upon the passage of each particle one information as to the size of the latter. Most often, there is performed a measurement of the resistivity of the particles in liquid medium (Coulter apparatus) or of their optical properties. In the latter case, the particle passes through an illuminated region, and the light absorbed or diffused is observed during its passage.

The illumination is effected by a single beam or by two coherent beams producing interference fringes, the passage of the particle before the network of fringes producing in the latter case a periodic change in the diffused light.

The frequency of this change is related to the speed of the particle, while the amount of the modulation is related to its size.

The known flow processes have the advantage of permitting study of the particles one by one thereby favoring the determination of granulometric curves. However, the drawbacks of the flow process, which consist in providing high dilution to avoid the simultaneous passage of two particles through the measurement zone, and the circulation of the suspension to be analyzed, may be incompatible with certain determinations, such as, particularly, the mechanism of aggregate formation. Moreover, the measurement cell often operates at high frequencies to permit the observation of a significant number of particles, thereby limiting the quantity of data obtained per particle, and involving errors of various types that cannot always be compensated by computation.

The batch processes comprise the simultaneous introduction of a large number of particles into a measurement cell, which provides batch information from which is determined the number, the dimensions and the distribution of the particles involved. The measurement techniques involved may be either mechanical, such as sedimentation, or primarily optical, such as diffractometry and nephelometry.

These processes have, compared to the known flow processes, the advantage of requiring only one simple preparation of the specimens to be analyzed, particularly when they make possible the analysis of poly-dispersed granular populations, which is to say formed by mixtures of several families of mono-dispersed particles, the simultaneous analysis of some of these families being possible by these processes. The batch processes permit, moreover, obtaining an immediate measurement representative of the mean of a large collection of particles. However, the information furnished by the cell is the composite of the elementary informations concerning each particle, and if these bits of information are not sufficiently complete or differentiated from each other, their analysis is difficult, variations in size interferring particularly with variations in numbers, particularly in batch optical processes. These known processes therefore give only results that are limited as to scope and precision, except by the use of difficult and costly measures, which thus considerably restrict the field of use.

It is in fact usual to count mono-dispersed populations, of a size distribution fairly well clustered about a normal mean value, in a satisfactory way, by a batch optical process in which the particles are illuminated by a single light beam, and the diffracted flux is measured in a particular solid angle called "stationary", so chosen that the diffracted flux there remains substantially stationary when the mean size of the particles to be counted varies within a certain range from its mean value. The measured flux is representative only of the number of particles to be counted, because it is independent of the variations in size of these particles.

This process is therefore applicable to the counting of poly-dispersed granulometric populations with only one important restriction. Indeed, considering the mixture of two mono-dispersed populations of different mean sizes, there is for each population one stationary solid angle, which would permit effectively to count the considered population if this population were single. So, for two populations there are two distinct such stationary solid angles. As a result, in each stationary solid angle will be measured a total flux equal to the sum of a first flux that is stationary as a function of the size of the population to which that solid angle corresponds, and of a second non-stationary flux as a function of the size of the other population. To be able to use the process, it is thus necessary to be able to know simultaneously the sizes of the two populations in question, and the same is true in the case of a mixture of more than two populations. The restriction of the use of this process is therefore that the sizes of all these populations must be known and, moreover, must remain simultaneously completely stable, which is not the case in a great number of practical situations.

Improvement in the results of the process can be provided by the use of supplemental measures determining the sizes at the same time as the numbers. However, the cost of the apparatus would then be excessive with respect to other methods, for comparable results.

The present invention has for an object to overcome these difficulties while giving access to batch information in which the influence of size and numbers is better differentiated than in known processes, to permit characterizing poly-dispersed granulometric populations or to determine the granulometric curves with greater precision, by simple calculations and under more economical conditions.

Figure 1:
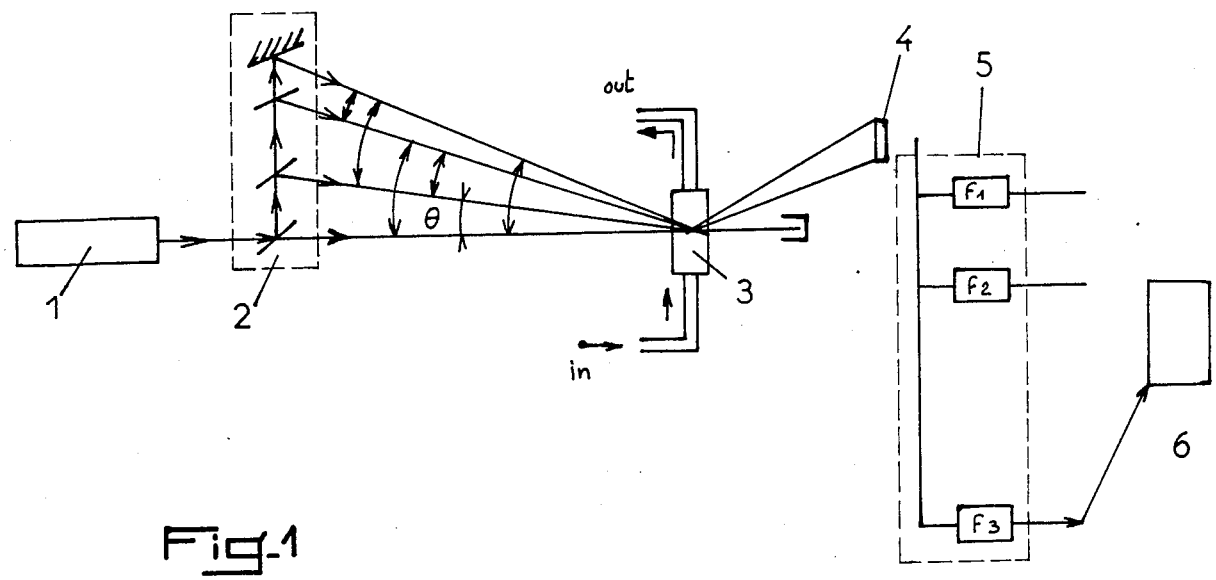
FIG. 1 is a schematic view in side elevation of an apparatus for practicing the process according to the invention.

It thus has for its object a batch interferential granulometric process applicable particularly to poly-dispersed biological particles, characterized by a combination of steps consisting in:

suspending the particles to be analyzed in a fluid in which they are distributed at random moving said particles and fluid with uniform speed through a fluid pathway including one measuring volume (3) in which the particles may be illuminated when they cross said volume illuminating said particles simultaneously by at least two beams of coherent light with convergent axes, beams produced by a light source (1) and a splitter (2), thus producing in the measuring volume (3) a network of interference fringes measuring by a photodetector (4) the light flux diffracted by said illumianted particles in at least one solid angle setting the concentration of said particles in said fluid so that at each instant a group of particles are simultaneously illuminated in said measuring volume setting the angles between said coherent beams, and thus the interference fringe distances, at values defined according to an iterative computation process setting the position and the limits of said solid angles as a function of the granulometric measurement to be made, these position and limits being obtained by said special iterative computation process involving also the said interference fringe distances using only the alternative components of the measurement signals representing the flux diffracted by said particles in said solid angles treating, when the particles are illuminated by more than two beams, these alternative components by a Fourier Analysis device (5) in order to separate the various frequencies which are present in these components treating the obtianed results in a treatment module (6) in order to calculate the sought granulometric characteristics.

Processes utilizing similar means, particularly means for performing a Fourier harmonic analysis on signals representing the diffracted flux created by particles illuminated by several coherent intersecting beams, are known, but they are used for velocimetry, which is the determination of the particle speed or of the distribution of the speeds of the moving particles. Such velocimetric processes may also be used in an extension of their original purpose for particle sizing but only if the sizes are homogeneous or the size distribution very narrow, and for measuring number densities when the size of the particles is known. In that field their accuracy is not high, these velocimetric processes being essentially different from that of the present invention not only by the results sought and obtained, but also by the combination of means employed. Particularly, their results are not influenced in a determinative way by the choice of the solid angle where the diffracted flux is collected and measured.

The interference of two coherent light beams of wavelength $\lambda$, whose axes intersect at an angle $\theta$, permits obtaining an interference fringe whose value is $\delta = \lambda/2 \sin(\theta/2)$ From the simultaneous interference of K beams with convergent axes, there are $l = K(K-1)/2$ different couples of beams which may be considered as combined in this condition, to which there correspond a maximum of l different angles $\theta$ and thus as many interference fringe values. Designating these values of interference fringes $\delta_1, \delta_2, -\delta_i \ldots$ and $\delta_l$, and considering V to be the speed of flow of the particles in front of the fringes, which is taken to be constant, it will be seen that to the various possible combinations of couples of bundles it corresponds l modulation frequencies on the diffracted flux equal to:

$$f_1 = V/\delta_1, f_2 = V/\delta_2 \ldots f_i = V/\delta_i \ldots \text{and } f_l = V/\delta_l.$$

From the simultaneous interference of all these beams the harmonic analysis of the resulting modulation leads to l frequencies $f_1, f_2, \ldots f_i, \ldots f_l$ and gives a corresponding amplitude for each. These amplitudes indicated by $e_1, e_2, \ldots e_i, \ldots$ and $e_l$ are a function of the numbers and sizes of the illuminated particles and of the solid angle of measurement of the diffracted flux.

This method therefore permits obtaining, in the measured signal, a number l of superposed separate data, from a single measurement in a single solid angle of collection, while in the absence of a fringe, as is usual in prior art methods, a measurement in l different solid angles would have been necessary to obtain the same amount of information.

Moreover, the obtained values $e_i$ distinguish better the effects of size from the effects of number than the continuous diffracted flux measurements in non-interferential batch processes. Thus, although the continuous diffracted flux varies proportionally to the number of illuminated particles when the latter are of uniform size, the alternative component of the flux modulated by the fringes varies, under the same hypothesis, proportionally not to the number but to the square root of the number of illuminated particles. A relative amplification of the effects of size relative to the effects of numbers may thus be usefully made, particularly to count poly-dispersed particles and for the determination of granulometric curves. Moreover, the variation of the modulation ratio of the diffracted light by a particle is a function of the relation of the size of the latter to the interference fringe, as well as to the angle from which the particle is observed.

Under certain simplified conditions, it is known that this modulation ratio varies according to the formula $$\frac{2 J_1\left(\frac{2\pi a}{\delta}\right)}{\frac{2\pi a}{\delta}}$$

in which
 $J_1$ is the first order Bessel function
 a is the radius of the particle
 $\delta$ is the interference fringe value.

Figure 2:
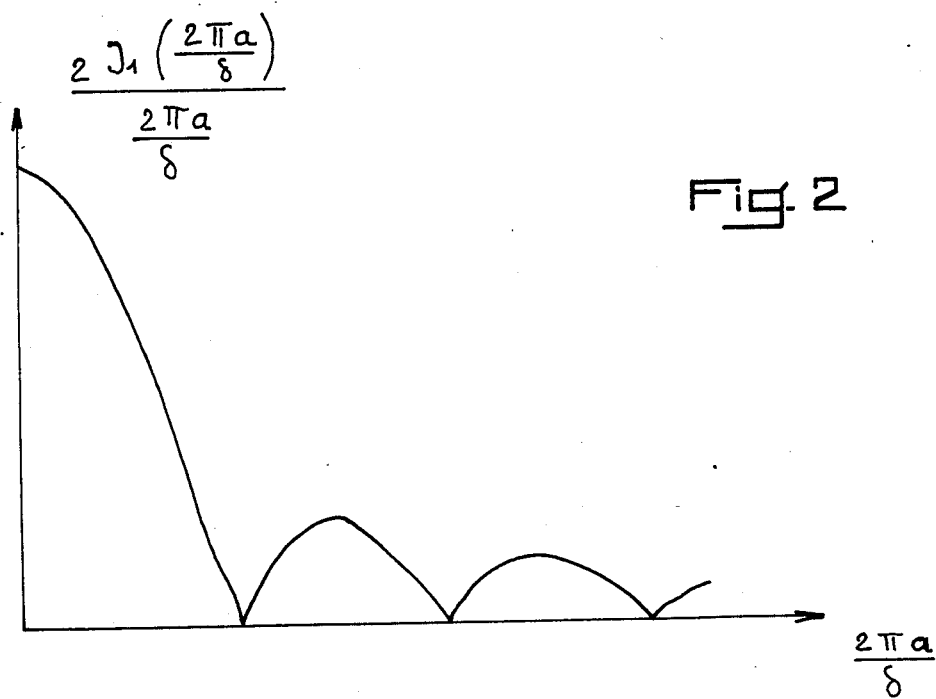
FIG. 2 shows the infuence of the ratio of the size of the particles to the interference fringe.

This formula, by way of example, is shown in FIG. 2. In the general case, the modulation ratio $V(a, \delta, s)$ is given by a more complex expression which involves, moreover, the angle of observation s. However, the formula given above shows in a simplified way that there are particular values of the ratio $a/\delta$ for which the modulation ratio will be zero or at least substantially near from zero, that is to say for a given interference fringe $\delta$, there exists particle sizes for which the diffracted flux will have practically no modulation, which means that the particles do not contribute to the formation of the alternative component of the diffracted modulated flux.

This property is particularly interesting in the case of analysis of poly-dispersed populations. In this case, the process according to the invention may be applied in a characteristic way by setting an interference fringe value so as to eliminate the influence of one population by annulling its contribution to the formation of the modulation of the diffracted flux, and using this interference fringe value in the computation of the associated solid angles to be used for the flux measurements.

One important characteristic of the invention, consists in using solid angles computed so that, for a given population size and for an associated fringe value, the alternative component of the flux, which is diffracted by said particles population, remains stationary when the size of the particles varies around a mean value.

In known non-interferential processes, similar stationary solid angles are also used, in which the continuous signal representing total diffracted flux remains stationary when the particle size varies around a mean value. But in the process according to the invention the stationarity is investigated only on the alternative component of the modulated signal measuring the diffracted flux, and the solid angles where this property exists are different from those where the total continuous signal remains stationary. This difference may be understood by reference to the influence, shown in FIG. 2 of the interference fringe related to the particle size on the modulation ratio.

The new stationary solid angles thus defined have the advantage of providing in certain cases precise information as to the count of the poly-dispersed particles, these data being directly separated from each other by virtue of the aforesaid discriminatory properties. These new stationary interferential solid angles thus permit simultaneously counting mono-dispersed mixtures of particles of different sizes, contrary to the prior art processes.

A characteristic example of the use of the process according to the invention concerns counting the figured elements of the blood, particularly simultaneously counting white corpuscles and platelets in the presence of stroma or lysed red corpuscles. In blood of normal composition comprising per mm$^3$ $N_B$=8,000 white corpuscles, $N_P$=300,000 platelets, and $N_S$=5,000,000 red corpuscles or stroma, a continuous stationary solid angle for the white corpuscles receives a diffracted flux from 50% of the white corpuscles, 7% of the platelets, and 43% of the stroma. Because this solid angle moreover is not stationary for the platelets or for the stroma, the flux measured in it does not permit direct counting of the white corpuscles.

A stationary solid angle for the white corpuscles, defined according to the invention for an optimum interference fringe value, receives, with the same ratio between $N_B$, $N_P$ and $N_S$, a diffracted flux whose alternative component comes from 99% of the white corpuscles, the influence of the other particles being negligible. Because in this solid angle, this component is independent of the variations of size of the white corpuscles, its amplitude directly represents their number despite the presence of other particles.

The process according to the invention may be used for the determination of a granulometric curve in the following manner:

Letting $a_1$ and $N_1$ represent the mean radius and the number of particles pertaining to class 1 and $a_2, N_2, \ldots a_j N_j$, and $a_n$ and $N_n$ the mean radii and the numbers of particles of classes 2, j, and n, one can cause to intersect K beams defining $l=K(K-1)/2$ harmonic frequencies, provided $l \geq n$.

From one signal solid angle for flux measurement, the Fourier harmonic analysis of the measured signal thus gives l values of amplitudes of different frequencies $e_1$, $e_2, \ldots, e_i \ldots e_l$ corresponding to the various frequencies $f_1, f_2, \ldots f_l$. The values $e_i$ are related to the numbers $N_j$ by relationships of the type:

$$F(e_i) = \sum_{j=1}^{j=n} a_{i,j} N_j$$

$F(e_i)$ being a function of $e_i$, and $a_{i,j}$ being a coefficient depending on the interference fringe value $\delta_i$ and on $a_j$ as well as on the position of the solid angle used.

For l values of frequencies (or of interference fringes) and a single solid measurement angle, there will therefore be used l equations such as Equation 1. If l is greater than n, it will suffice to use n equations, among the l available, so as to be able to calculate the values of $N_j$. The best choice of these n equations is that which will provide a matrix connecting the $N_j$ to $F(e_i)$ so as to be the most diagonal possible, which may be written in the matrix form $$|F(e_i)| = M \cdot |N_j|$$

and $$|N_j| = M^{-1} |F(e_i)|$$

$M^{-1}$ being the most diagonal possible

When using in an analogous fashion no longer a single solid measurement angle, but a number m of such angles, there will be obtained a number l.m of separate equations like equation 1, from among which can be chosen n to provide an optimum matrix $M_o^{-1}$ which will be, like the preceding one, the most diagonal possible.

It will be understood that the process of the present invention is potentionally more discriminatory than the non-interferential batch processes by virtue of the fact that among the choice of conditions for its use, there are available two degrees of freedom instead of a single one, namely, on the one hand, the number of solid measurement angles used, and, on the other hand, the number of separate frequencies used, it being understood that the choice of the positions of these solid angles and of the values of the frequencies themselves, is also available. By means of a judicious choice of the whole of these parameters, one can immediately achieve information either directly representative of the granulometric characteristics sought, or connected to the same by a system of equations easier to solve in a sufficiently precise way than in other processes, the treatment module 6 shown in FIG. 1 being thus adapted to be quite simplified.

To find optimum conditions of use of the process for the determination of a granulometric curve, that is to say to find the best combination of frequencies and solid angles to be used with the granulometric classifications in question, the computation process comprises first the programming in the computer, in a conventional manner, the calculations permitting determining the flux diffracted by the particles in all directions and taking into account the intersection of the pairs of incident beams from which the interference arises.

Then the repeated use of this program is programmed by causing the interference fringe values and the limits of the sought angles in question to vary, for each granulometric class, so as to scan systematically all the conceivable conditions and compare the results obtained so as to arrive at the best conditions.

Thus, the computation process requires indications relative, on the one hand, to the formulas to be used for the calculation of the alternative flux diffracted, and relative, on the other hand, to the interference fringe values at the outset to be used to begin the computation, the programming operation itself being adapted to be performed in known manner.

The alternative flux diffracted in a region of solid angle $\Omega$ by a particle of a radius a for a value $\delta$ of interference fringe may be calculated according to the general expression $$E(a) = \int_\Omega I(a,s) \cdot V(a,\delta,s) \cdot ds$$

in which
I (a,s) is the intensity diffracted by a particle of radius a at an observation angle s, this angle completely sweeping the solid angle $\Omega$, when this particle is illuminated by two beams producing the interference fringe $\delta$
V (a,$\delta$,s) is the rate of modulation of the diffracted light, which is a function, as indicated above, of the three parameters a,$\delta$,s These elements I (a,s) and V (a,$\delta$,s) may be calculated by formulas of approximation proposed particularly by
Farmer (Applied Optics, November, 1972)
Atakan & Jones (Applied Optics, January, 1982)
Bachalo (Applied Optics, February, 1980)

As a first approximation, one can use the following formulas:

$$I_{s1,s2}(a) = \frac{\pi a^2}{2} \int_{kas_1}^{kas_2} \frac{4 [J_1(x)]^2}{x} dx$$

wherein $k=(2\pi/\lambda)$ $\lambda$ wavelengths of the light used
$I_{s1,s2}$ (a) is the intensity of the light diffracted in a zone limited by the two extreme angles $s_1$ and $s_2$
$J_1$ (X) is the first order Bessel function $$V(a, \delta) = \frac{2 J_1\left(\frac{2\pi a}{\delta}\right)}{\frac{2\pi a}{\delta}}$$

as indicated above. As to the choice of interference fringe values, it is appropriate to use as a starting value twice the radius of the particle, namely $\delta=2a$ and then preferably to examine the higher values of $\delta$. However, in case of poly-dispersed particles, it is necessary to note two particularities:
on the one hand, if it is desired to effect counting by eliminating the influence of a population of, for example, turbulence, one can preferably use a value $\delta=1.64a$
on the other hand, it is possible, as shown by the example hereinafter, that an interference fringe value adapted to one class of particles is equally applicable to another class of smaller size.

The next stage of calculation consists in determining the relations such as those of Equation 1, and to compare their interest with a view toward the formation of an optimum calculation matrix, while varying the parameters of interference fringe and of position and of extent of the solid angles.

Here again, according to the simplified hypotheses used, one can use more or less complicated formulas. For a good approximation, one can use equations such as the following:

$$\overline{S_i}^2 = \sum_{j=1}^{j=n} (E_i{}^j)^2 N_j \qquad \text{Equation 2}$$

or
$\overline{S_i}^2$ is the mean value of the square of the alternative flux of frequency fi received over the solid measurement angle
$E_i{}^j$ is the value calculated as seen above for the expression E (a) with a value $\delta^i$ of interference fringe corresponding to the frequency fi for a particle of the class j having a mean radius $a_j$
Nj is the number of particles in the class j It will be noted that this formula permits achieving the result stated above, in which $S_i$ varies as $\sqrt{N_j}$, or more exactly $\overline{S_i}^2$ as Nj.

These elements permit the use of the process in a satisfactory manner of the determination of granulometric curves, the calculations being conducted using the mean dimensions of the particles, that is to say using the assumption that, in each class of particles, these all have the mean size of the class.

One then seeks, for each class of particle of mean radius $a_j$ a couple ($\delta,\Omega$) such that the expression E (a) will be a maximum for $a=a_j$ and as small as possible for a $\neq a_j$, which, as is shown by Equation 2, will result in the most diagonal matrix.

Of course, one can also refine the computation to determine a granulometry with the highest precision by calculating not only E ($a_j$) from the mean dimension $a_j$, but more particularly the mean value assumed by E (a) in the interval corresponding to class j, by integrating E (a) across this interval. One can then take account of the granulometric distribution of the particles of the class j, assuming it is known in advance, to calculate a mean value of E (a) more pertinent to this class j.

All these processes for calculation are given by way of example, without thereby introducing a limitation.

For counting purposes, or for improved granulometry, the computation process may be so oriented as to determine the stationary solid angles evoked above.

To this end, the computation process leading to the determination of said solid angles, for a given population, and for an associated interference fringe value, is defined in order to determine solid angles in which the alternative component of the flux diffracted by the particles remains stationary when the size of the particles varies around a normal value.

In that purpose the computation process leading, for a particular given population of particles, and for an associated interference fringe value to the determination of one solid angle is defined in order to determine one solid angle in which the alternative component of the flux diffracted by the particles is proportional to the volume of these particles, that means that for such a solid angle, the expression $E(a)/a^3$ remains stationary when the diameter of the particles varies between the extreme values for this population.

The following example, calculated according to the approximate formulas indicated, illustrates an instance of use of the invention. One seeks to count three families or classes of particles intimately mixed, knowing that they are characterized by the following granulometric ranges:

Family 1: diameters of 2 to 3 μm   Number $N_1$
Family 2: diameters from 5 to 6 μm   Number $N_2$
Family 3: diameters of 10 to 20 μm   Number $N_3$ The calculation leads, with $\lambda=0.6328$ (helium-neon laser) to the following dimensioning:

Three solid angles or "windows" are determined, each being alternatively stationary for one of the three families.

Figure 3:
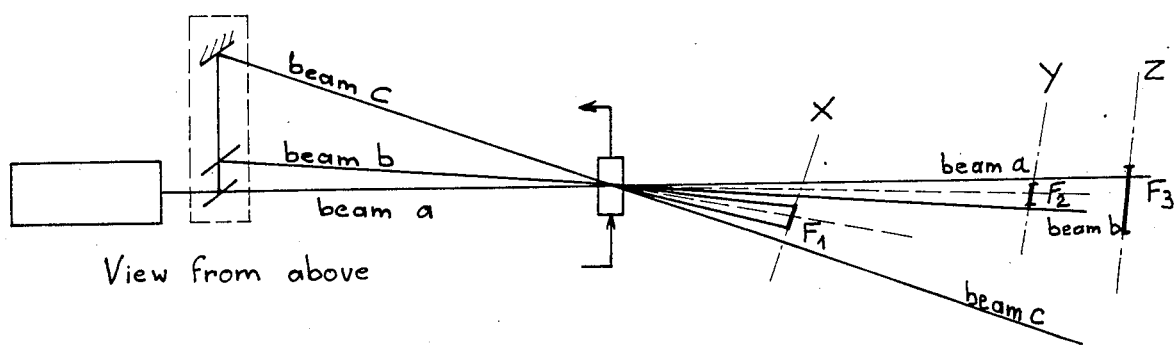
FIG. 3 shows an example of application of the process.
Figure 3:
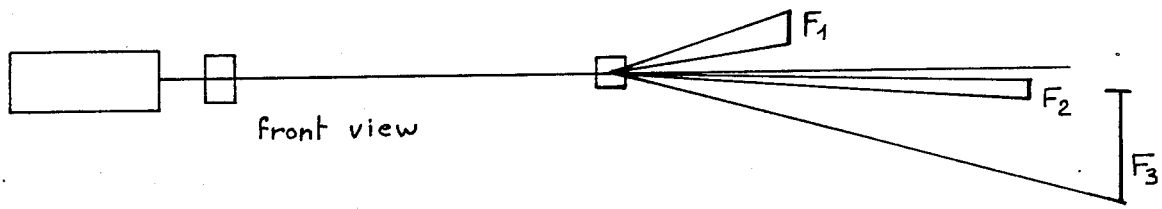
Figure 3:
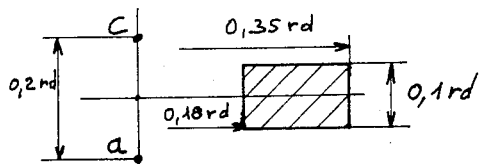
Figure 3:
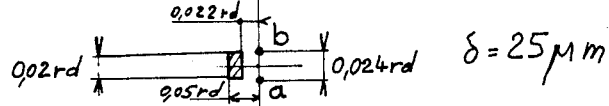
Figure 3:
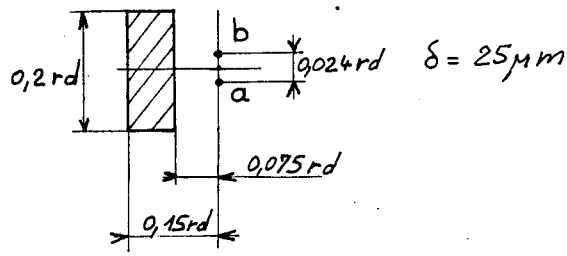

The window $F_1$ which is invariable for the first family corresponds to an interference fringe value of 3.2 μm. Its position is given in FIG. 3.

To windows $F_2$ and $F_3$ (see FIG. 3) which are invariable for the respective families 2 and 3, correspond the same value of interference fringe, 25 μm. One thus reaches the case set forth above in which the interference fringe associated with family 3 will be equally useful for family 2, which is of interest for simplifying the apparatus for practicing the method.

What is claimed is:

1. Process for batch interferential granulometry useful particularly for poly-dispersed biological particles, characterized by a combination of steps consisting in:
    suspending the particles to be analyzed in a fluid in which they are distributed at random
    moving said particles and fluid with uniform speed through a fluid pathway including one measuring volume in which the particles may be illuminated when they cross said volume
    illuminating said particles simultaneously by at least two beams of coherent light with convergent axes, thus producing in the measuring volume a network of interference fringes
    measuring the light flux diffracted by said illuminated particles in at least one solid angle
    setting the concentration of said particles in said fluid so that at each instant a group of particles are simultaneously illuminated in said measuring volume
    setting the angles between said coherent beams, and thus the interference fringe distances, at values defined according to an interative computation process
    setting the position and the limits of said solid angles as a function of the granulometric measurement to be made, these position and limits being obtained by said special iterative computation process involving also the said interference fringe distances
    using only the alternative components of the measurement signals representing the flux diffracted by said particles in said solid angles
    treating, when the particles are illuminated by more than two beams, these alternative components by a Fourier Analysis device in order to separate the various frequencies which are present in these components
    treating the obtained results in a treatment module in order to calculate the sought granulometric characteristics.

2. Process according to claim 1, in which the computation process leading to the determination of said solid angles, for a given population, and for an associated interference fringe value, is defined in order to determine solid angles in which the alternative component of the flux diffracted by the particles remains staitonary when the size of the particles varies around a normal value.

3. Process according to claim 1, characterized by setting an interference fringe value so as to eliminate the influence of one popoulation by annulling its contribution to the formation of the modulation of the diffracted flux, and using this interference fringe in the computation of the associated solid angles to be used for the flux measurements.

4. Process according to claim 1, in which the computation process leading, for a particular given population of particles, and for an associated interference fringe value, to the determination of one solid angle is defined in order to determine one solid angle in which the alternative component of the flux diffracted by the particles is proportional to the volume of these particles, that means that for such a solid angle, the expression $E(a)/a^3$ remains stationary when the diameter of the particles varies between the extreme values for this population.

* * * * *